United States Patent [19]

Kaufman et al.

[11] Patent Number: 4,750,491
[45] Date of Patent: Jun. 14, 1988

[54] TREPHINE AND METHOD

[75] Inventors: Herbert E. Kaufman; Marguerite B. McDonald, both of New Orleans, La.

[73] Assignee: Allergan, Inc., Irvine, Calif.

[21] Appl. No.: 670,396

[22] Filed: Nov. 8, 1984

[51] Int. Cl.$^4$ .................................................. A61B 17/32
[52] U.S. Cl. .................................................... 128/305
[58] Field of Search ............... 128/305, 305.1, 751, 128/310, 752, 753, 754; 30/287, 300, 310

[56] References Cited

U.S. PATENT DOCUMENTS

| | | | |
|---|---|---|---|
| 1,043,408 | 11/1912 | De Vilbiss | 128/305.1 |
| 1,837,067 | 12/1931 | Reiter | 128/92 V |
| 2,249,906 | 7/1941 | Longoria | 128/305 |
| 2,473,968 | 6/1949 | Paton | 128/305 |
| 2,818,852 | 1/1958 | Kugler | 128/305 |
| 3,384,086 | 5/1968 | Rocha-Miranda et al. | 128/305 |
| 4,205,682 | 6/1980 | Crock et al. | 128/305 |
| 4,417,579 | 11/1983 | Soloviev et al. | 128/305 X |
| 4,423,728 | 1/1984 | Lieberman | 128/310 |
| 4,526,171 | 7/1985 | Schachar | 128/305 |

FOREIGN PATENT DOCUMENTS

| | | | |
|---|---|---|---|
| 1185860 | 4/1985 | Canada | 128/317 |
| 2487667 | 2/1982 | France | 128/305.1 |
| 545342 | 2/1977 | U.S.S.R. | 128/305.1 |

Primary Examiner—Robert P. Swiatek
Assistant Examiner—David L. Tarnoff
Attorney, Agent, or Firm—Gordon L. Peterson

[57] ABSTRACT

A trephine for cutting a groove in the cornea of an eye comprising a fixation member and first and second shafts having blades mounted thereon. The fixation member includes a bearing, and the shafts are sequentially receivable within the bearing. The fixation member can be affixed to the eye, and the shafts, when received in the bearing, are rotatable in the bearing so that the blades carried by the shafts can make cuts in the cornea. By making cuts in the cornea which intersect, a segment of the cornea can be removed to provide the groove.

33 Claims, 4 Drawing Sheets

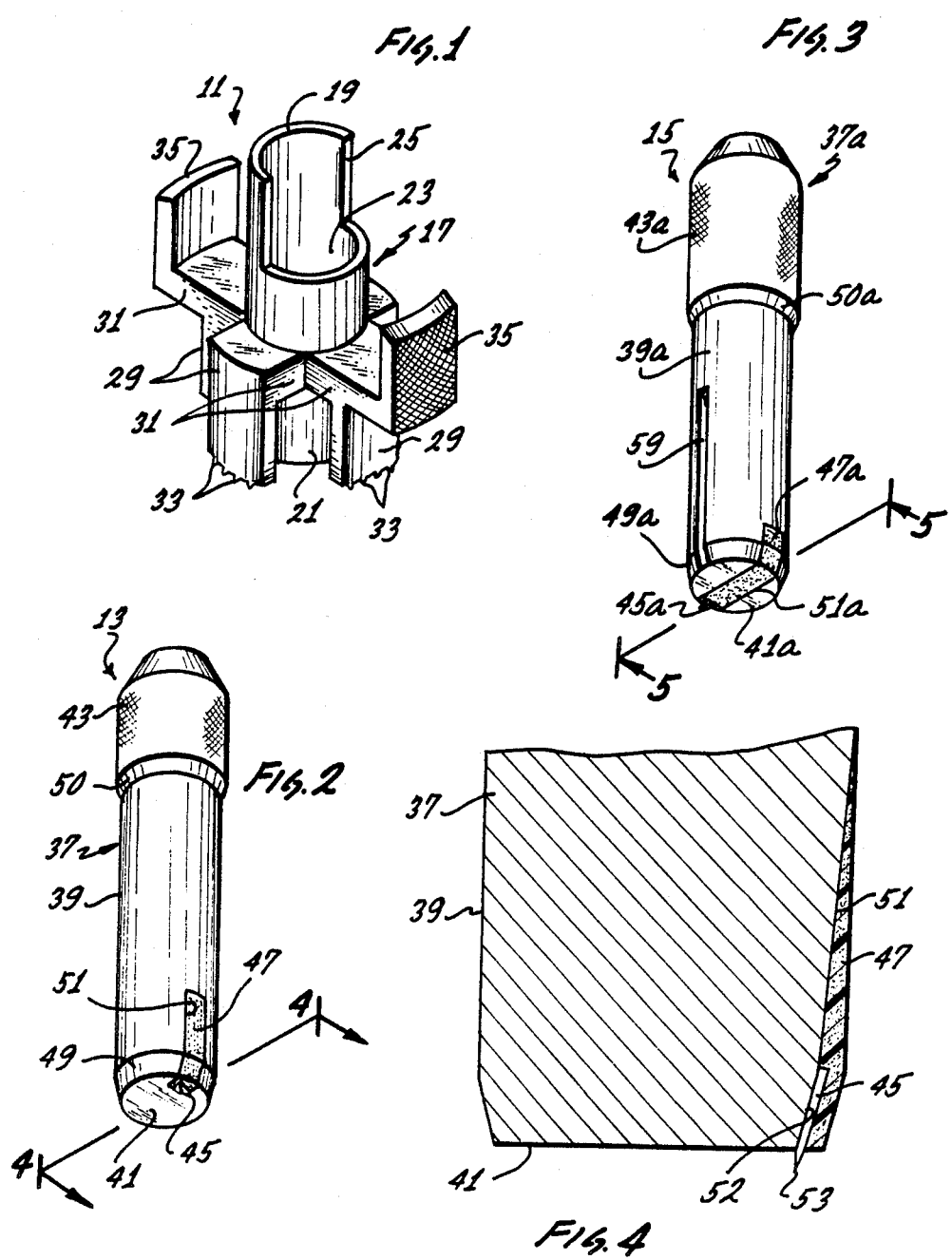

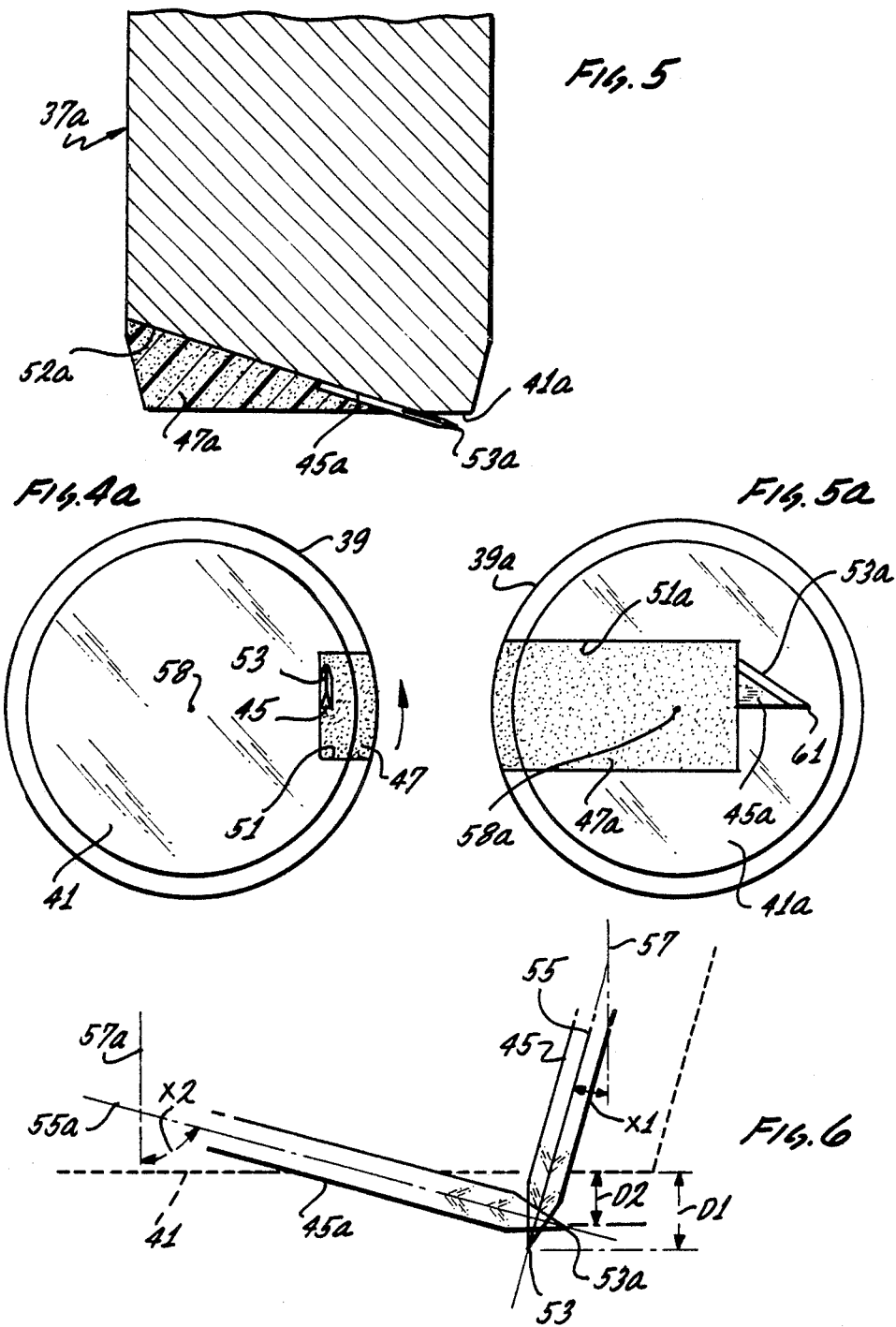

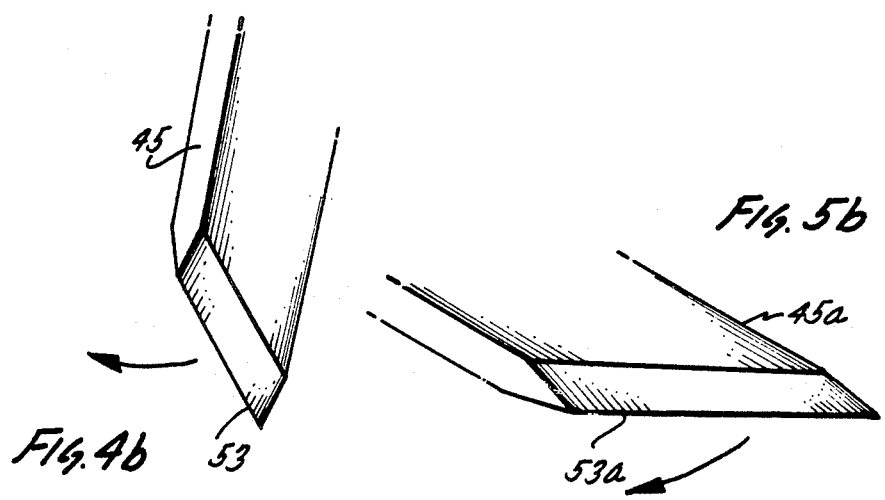
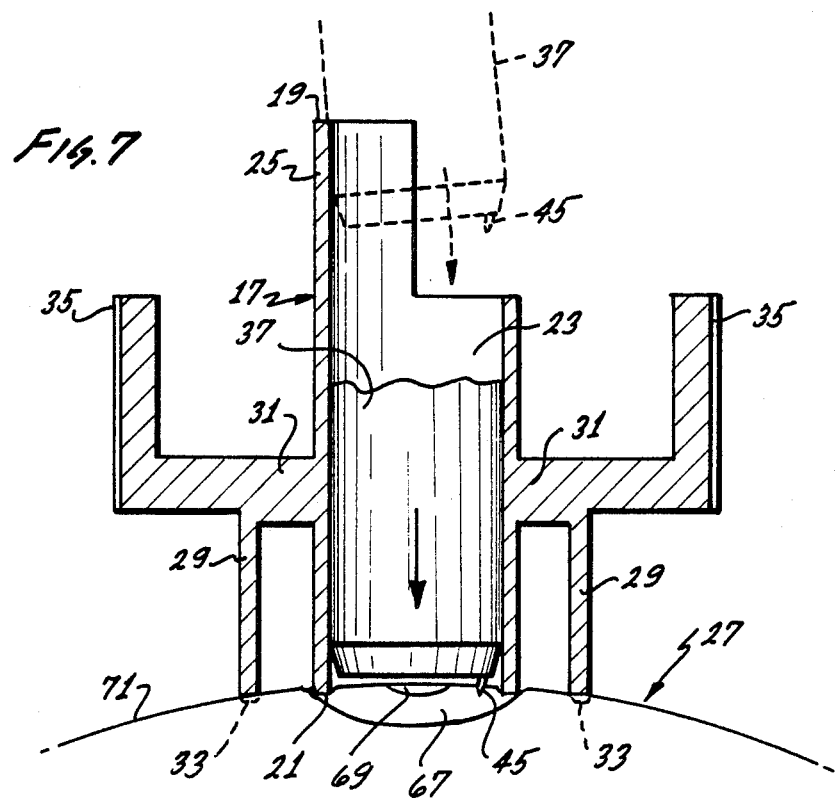

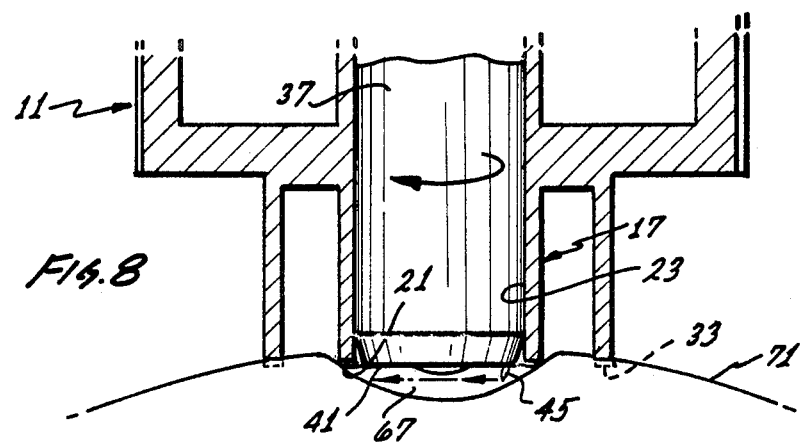
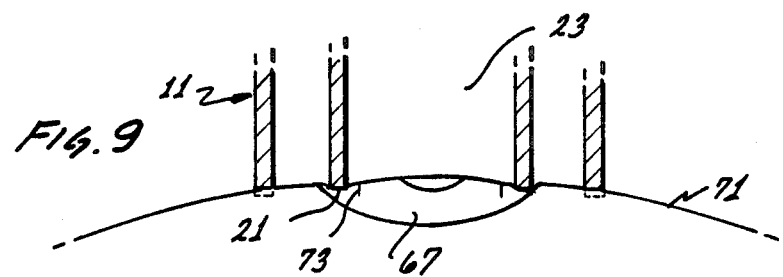
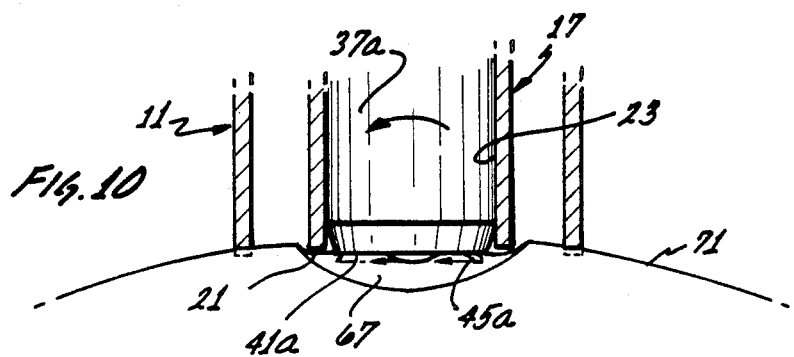
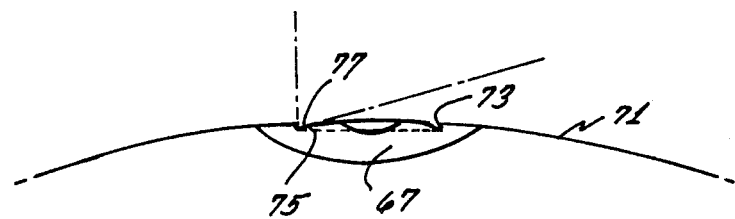

TREPHINE AND METHOD

BACKGROUND OF THE INVENTION

In the medical treatment of certain conditions of the eye, it is sometimes necessary or desirable to form a groove in the cornea. The groove may be formed near the outer perimeter of the cornea so that replacement corneal tissue can be tucked into the groove and sewed in place.

The groove, which may be annular, can be formed by making two intersecting cuts in the cornea. These cuts must be made very carefully to a shallow depth which may be, for example, about 0.2 to about 0.4 millimeters (mm). It is extremely difficult to carefully and accurately make shallow incisions on the corneal surface due to the non-rigid nature of the eye.

A trephine can be used to make an incision in the cornea. One prior art trephine includes a hollow cylinder having a cylindrical razor blade at one end for forming a generally vertical cut in the periphery of the cornea for 360 degrees. Scissors are then used to manually form an angle cut in the cornea which intersects the vertical cut, and the resulting segment can be removed from the cornea to provide a groove. Unfortunately, it is exceedingly difficult to accurately control the scissors-cutting operation, and it takes a relatively long time to complete the scissors cut.

Lieberman U.S. Pat. No. 4,423,728 discloses a trephine which can make both of the cuts in the cornea, thereby eliminating the need for a scissors cut. However, this trephine is very complex and provides for numerous adjustments of the blade which introduce a possibility of human error in the corneal-cutting procedure.

SUMMARY OF THE INVENTION

This invention provides a trephine of simple construction which eliminates many of the possibilities for human error in the corneal-cutting procedure. The concepts of this invention can be embodied in a trephine which comprises a fixation member and first and second shafts, with each of the shafts having a blade mounted thereon. The fixation member must be fixable to the eye and support the shafts for rotation. For these purposes, it includes suitable means cooperable with the eye for fixing the fixation member to the eye and a bearing having a passage for receiving and mounting the shafts for rotation about a rotational axis.

In use, the first shaft is inserted into the bearing to a first axial position in which the associated blade is in contact with the cornea, and the shaft is then rotated to form a first cut in the cornea. The first shaft is then withdrawn, and the second shaft is inserted into the bearing to a second axial position and rotated to form a second cut which intersects the first cut. This provides a severed corneal segment which can be removed to provide a groove in the cornea.

Several factors combine to enable the trephine of this invention to accurately and rapidly provide the desired cut. For example, each of the blades is mounted on the associated shaft, with the cutting edge of the blade projecting a fixed distance beyond the end wall of the shaft. In use, the shaft can be axially advanced into the bearing until the end wall of the shaft engages the cornea. Therefore, the depth of cut is accurately related to the fixed distance that the blade projects beyond the end wall. This also reduces the likelihood of human error in establishing the depth of the cut. In addition, fixedly mounting the blade contributes to simplicity in the construction.

The fixation member also contributes to the accuracy of the results by being accurately fixable to the eye. Although various forms of fixation can be employed, complexity is reduced by eliminating the vacuum fixation techniques of the prior art in favor of teeth on the fixation member located to engage the sclera of the eye. The teeth can advantageously be provided on legs coupled to the bearing and located radially outwardly of the bearing.

The features of this invention may be used to form one or more cuts in the cornea. If the cuts are to define a segment which can be removed from the cornea to form a groove, then the blades on the two shafts must be appropriately oriented relative to the associated shaft to perform this function. Alternatively, if the features of this invention are to be utilized to form, for example, only a single cut, then only a single shaft is needed, and the blade used for that cut must have an appropriate orientation to provide the desired cut.

Although the exposed portion of the blade can be constructed of different materials, it is preferably a diamond. A diamond is preferred because of its sharpness and its tendency not to dull. To protect the diamond from damage, the exposed portion of the blade preferably lies entirely within the perimeter of the peripheral wall of the shaft as viewed in a direction perpendicular to the end wall of the shaft. Also, the bearing only partially circumscribes the passage of the bearing at the outer end of the bearing to permit insertion of the shaft in the passage with reduced likelihood of damage to the blade.

The shaft and blade form a knife. The blade is preferably fixedly mounted on the shaft by a mounting body of plastic. The mounting body can advantageously be retained in a groove of the shaft which opens at the end wall of the shaft. In order for the blade to make the desired vertical cut in the cornea, the blade is preferably adjacent the peripheral wall of the shaft, and the projecting portion of the blade is inclined radially inwardly. Because of the non-rigid nature of the cornea, this radial inclination of the blade is necessary to get an essentially vertical cut.

The invention, together with additional features and advantages thereof, may best be understood by reference to the following description taken in connection with the accompanying illustrative drawing.

BRIEF DESCRIPTION OF THE DRAWING

FIGS. 1–3 are isometric views illustrating, respectively, one form of fixation member and first and second knives constructed in accordance with the teachings of this invention.

FIG. 4 is an enlarged, fragmentary sectional view taken generally along line 4—4 of FIG. 2.

FIG. 4a is a bottom plan view of the knife of FIG. 2.

FIG. 4b is an isometric view of the blade used in the knife of FIG. 2.

FIG. 5 is an enlarged, fragmentary sectional view taken generally along line 5—5 of FIG. 3.

FIG. 5a is a bottom plan view of the knife of FIG. 3.

FIG. 5b is an isometric view of the blade shown in FIG. 3.

FIG. 6 is a schematic elevational view, with the blades of the two knives superimposed to show their relative orientations.

FIG. 7 is a sectional view of the trephine affixed to the sclera, with the shaft as shown in dashed lines being inserted into the bearing and as shown in full lines almost fully axially advanced into the bearing.

FIGS. 8-10 are views similar to FIG. 7 illustrating the steps in making successive cuts into the cornea using two different knives.

FIG. 11 is an elevational view of a portion of the eye showing the groove cut therein.

DESCRIPTION OF THE PREFERRED EMBODIMENT

In the illustrated embodiment, the trephine includes a fixation member 11 (FIGS. 1 and 7) and one or more knives 13 and 15 (FIGS. 2 and 3). Although the fixation member 11 may be of various different constructions, in the embodiment illustrated, it includes a bearing in the form of an elongated cylindrical sleeve 17 having an outer end 19, an inner end 21, and an axial cylindrical passage 23 extending longitudinally through the sleeve. The sleeve 17, which may be considered as forming a peripheral wall around the passage 23, only partially circumscribes the passage at an outer end portion of the sleeve. More specifically, the sleeve 17 includes a semi-cylindrical section 25 adjacent its outer end 19. The inner end 21 of the sleeve 17 is annular.

The fixation member 11 includes means cooperable with a human eye 27 (FIG. 7) for fixing the fixation member to the eye. In the illustrated embodiment, such means includes four axially extending legs 29 equally spaced circumferentially and joined to the sleeve 17 by webs 31 which extend radially outwardly from the sleeve. The legs 29 lie radially outwardly of the sleeve 17 and terminate in teeth 33. Except for the teeth 33, the legs 29 terminate in essentially the same plane as the inner end 21.

To facilitate manually grasping the fixation member 11, two of the opposite legs 21 extend radially outwardly beyond the associated legs 29 and are joined to upwardly extending knurled tabs 35. As shown in FIGS. 1 and 7, the semi-cylindrical section 25 opens in the direction of one of the tabs 35 and extends axially beyond the tabs. In this embodiment, the fixation member 11 is integrally constructed of a suitable metal.

Although one or more of the knives can be provided, in this embodiment of the invention, the knives 13 and 15 are provided. The knives 13 and 15 are similar and, except to the extent shown or described herein, may be identical. Portions of the knife 15 corresponding to portions of the knife 13 are designated by corresponding reference numerals followed by the letter "a".

The knife 13 includes an elongated metal shaft 37 having a peripheral wall 39, an end wall 41 and a driving portion 43 for use in rotating the shaft, a blade 45, and a mounting body 47 for fixedly mounting the blade on the shaft. The shaft 37 has a conical portion 49 adjacent the end wall 41, and the peripheral wall 39 between the driving portion 43 and the conical portion 49 is essentially cylindrical. The driving portion 41 is radially thickened and is adjacent the end of the shaft 37 remote from the end wall 41. The shaft 37 has a shoulder 50 at the inner end of the driving portion 43.

The shaft 37 has a groove 51 (FIGS. 2, 4 and 4a) which opens at the end wall 41 and the peripheral wall 39 and which contains the mounting body 47. The groove 51 has an inclined inner wall 52 which is inclined radially inwardly as it extends axially toward the end wall 41, and a lower portion of the inner wall adjacent the end wall 41 is more sharply inclined radially inwardly. The mounting body 47 may be, for example, a suitable plastic which will fixedly bond the blade 45 to the shaft 37 in a predetermined orientation. The blade may lie along, and be supported by, the lower portion of the wall 52. The blade 45 is fixedly mounted in the sense that it cannot be moved with respect to the shaft 37 without deforming the blade.

The blade 45 is elongated and has a cutting edge 53 exposed beneath the end wall 41. Although the blade 45 can be of different constructions, in the embodiment illustrated, it is in the form of a straight linear member, and it is constructed of a diamond.

The extent to which the cutting edge 53 extends beyond the end wall 41, and the orientation of the blade 45 can be varied to accommodate particular cutting requirements. However, generally, the blade 45 will project only a short fixed distance beyond the end wall 41, and in the embodiment illustrated, a distance D1 (FIG. 6) from the cutting edge 53 to the end wall 41 is about 0.41 mm.

The angular orientation of the blade 45 may also be varied. However, if it is desired to use the blade 45 to obtain an essentially vertical cut in the cornea, it has been found necessary to incline at least the exposed portion of the blade radially inwardly. If this is not done, a vertical cut is not obtained in the cornea, and this is believed to be due to the unusual, non-rigid nature of the cornea. Although the angle of incline X1 (FIG. 6) can be selected depending upon the results desired, the angle of incline may be, for example, 15 degrees to 30 degrees. In the embodiment shown, the angle of incline X1 is 15 degrees. More specifically, the angle X1 is the acute angle formed by the axis 55 of the blade 45 and a reference line 57 which is parallel to the longitudinal axis 58 of the shaft 37. The cutting edge 53 is short, linear and extends generally tangentially to the direction of rotation as viewed in FIG. 4a.

Except for the presence of a pair (only one being shown in FIG. 3) of diametrically opposed, longitudinal grooves 59 in the peripheral wall 39a, a slight lengthening of the driving portion 43a and a different shape and orientation of the groove 51a, the shaft 37a may be identical to the shaft 37. The groove 51a preferably extends almost completely across the end wall 41a, and the groove has an inclined wall 52a as shown in FIG. 5. The mounting body 47a, like the mounting body 47, fills the groove in which it is positioned and has an appropriate contour to accomplish this objective.

The blade 45a may lie along, and be supported by, the wall 52a as shown in FIG. 5 and project from the mounting body 47a and beyond the end wall 41a. The blade 45a terminates in an inclined cutting edge 53a as shown in FIG. 5a, and projects to a point 61. The blade 45a projects a fixed distance D2 beyond the end wall 41a. The distance D2 is less than the distance D1 and may be, for example, about 0.25 mm.

Although the blade 45a can extend at different angles, if it is to be used in combination with the blade 45 for groove-cutting purposes, it should be inclined radially outwardly at an angle X2 which, in this embodiment, is 75 degrees. More specifically, the angle X2 is defined by the axis 55a of the blade 45a and a reference line 57a which is parallel to the axis 58a of the shaft 37a. As shown in FIG. 6, with the blades 45 and 45a superimposed, the blades overlap such that the cutting edge 53 extends below the cutting edge 53a, and the cutting edge 53a extends radially outwardly beyond the cutting edge 53. As shown in FIG. 6, the blades 45 and 45a have different orientations with respect to the associated axes 58 and 58a.

To protect the blades 45 and 45a from damage, they both lie entirely within the perimeter of the associated peripheral wall 39 as viewed in a direction perpendicular to the associated end wall 41 and 41a. As shown in FIGS. 4a, 5a and 6, the cutting edges 53 and 53a lie adjacent the associated peripheral walls 39 and 39a.

To use the trephine of this invention, the fixation member 11 is placed over the eye 27 as shown in FIG. 7. Specifically, the inner end 21 of the sleeve 17 is brought into generally coaxial alignment with the cornea 67, and the pupil 69 and the teeth 33 are pushed slightly into the sclera 71 to fix the fixation member 11 to the eye 27 with the inner end 21 of the sleeve 17 engaging the cornea 67. During the placement of the fixation member 11, the fixation member can be manually grasped by the tabs 35 and retained in this fashion during the procedure.

The shafts 37 and 37a are sized to be slidably and rotatably received within the passage 23 of the sleeve 17 as shown in FIG. 7 for rotation about a rotational axis which is essentially coincident with the axes 58 and 58a, respectively. More specifically, the shaft 37 is introduced into the passage 23 from the outer end 19 as shown in dashed lines in FIG. 7, with the blade 45 remote from the section 25 so as to avoid damaging the blade by contacting it against the outer end 19. The passage 23 slidably receives the shaft 37, and movement of the shaft 37 downwardly in the passage 23 can continue to an axial position (FIG. 8) in which the end wall 41 of the shaft 37 is out of the sleeve 17 and engages the cornea 67 with some slight force deemed appropriate by the surgeon, and the driving portion 43 is above the sleeve 17 so that it can be manually grasped to rotate the shaft. As shown in FIG. 8, forcing of the end wall 41 against the cornea tends to push the cornea away from the inner end 21 of the sleeve 17. In this axial position, the blade 45 enters the cornea 67 for a distance which is equal to, or directly related to, the fixed distance that the blade 45 projects beyond the end wall 41. Accordingly, manual rotation of the shaft 37 about the axis 58 for one revolution causes the blade 45 to make a first annular cut 73 (FIGS. 9 and 11) in the cornea 67. The cut 73 is essentially vertical.

The shaft 37 is then withdrawn from the passage 23, and the shaft 37a is inserted into the passage to the axial position shown in FIG. 10 which may be identical to the axial position of the shaft 37 as described above. Thus, the end wall 41a is out of the sleeve 17 and engages the cornea 67 to push the cornea away from the inner end 21 and to cause the blade 45a to enter the cornea for a distance which is equal to, or directly related to, the fixed distance that the blade 45 projects beyond the end wall 41a. The shaft 37a is manually rotated within the sleeve 17 about the axis 58a for one revolution to form a second cut 75 in the cornea 67. The shaft 37a is then withdrawn from the passage 23, and the fixation member 11 is removed from the eye 27. The cuts 73 and 75 define an annular segment of the cornea which may be removed to define a groove 77 as shown in FIG. 11. The shoulders 50 and 50a are engageable with the outer end 19 to prevent the shafts 37 and 37a from being advanced too far into the passage 23.

Although an exemplary embodiment of the invention has been shown and described, many changes, modifications and substitutions may be made by one having ordinary skill in the art without necessarily departing from the spirit and scope of this invention.

We claim:

1. A trephine for making a cut in the cornea of an eye, said trephine comprising:
 a fixation member including a bearing and means cooperable with the eye for fixing the fixation member to the eye;
 a shaft having a peripheral wall, an end wall and a driving portion for use in rotating the shaft;
 a blade having a cutting edge;
 means for mounting the blade on the shaft with the blade projecting a fixed distance beyond the end wall and with the cutting edge at least partially exposed;
 said shaft being rotatable in said bearing about a rotational axis; and
 the shaft being positionable in the bearing in an axial position in which the end wall is out of the bearing and engageable with the cornea and the driving portion can be driven whereby the shaft can be rotated in said axial position to cause the blade to form a first cut in the cornea having a depth which is related to said fixed distance.

2. A trephine as defined in claim 1 wherein said cooperating means includes teeth on the fixation member located to engage the sclera of the eye and cooperate therewith to fix the fixation member to the eye.

3. A trephine as defined in claim 1 wherein said fixation member includes a plurality of legs coupled to the bearing and adapted to extend toward the sclera radially outwardly of the bearing and said legs terminate in a plurality of teeth engageable with the sclera.

4. A trephine as defined in claim 1 wherein said bearing has a peripheral wall and a passage extending through the bearing for receiving the shaft, said bearing has inner and outer ends, and said peripheral wall only partially circumscribes the passage at an outer end portion of the bearing.

5. A trephine as defined in claim 4 wherein said fixation member includes a plurality of legs coupled to the peripheral wall and adapted to extend toward the sclera radially outwardly of the peripheral wall and said legs terminate in a plurality of teeth engageable with the sclera.

6. A trephine as defined in claim 1 wherein said mounting means includes a mounting body retained on said shaft and said blade is fixedly embedded in the mounting body.

7. A trephine as defined in claim 6 wherein said shaft has a groove opening at the end wall and said mounting body is retained in said groove.

8. A trephine as defined in claim 1 wherein at least said cutting edge of the blade is formed of a diamond.

9. A trephine as defined in claim 1 wherein the cutting edge has a first orientation with respect to the rotational axis and the shaft is removable from the bearing, said trephine includes a second shaft having an end wall and receivable in said bearing when the first-mentioned shaft is removed from the bearing, said second shaft being rotatable generally about said rotational axis, a second blade having a second cutting edge and being fixedly mounted on said second shaft and projecting beyond the end wall of the second shaft, said second cutting edge having a second orientation with respect to the rotational axis, said first and second orientations being different.

10. A trephine as defined in claim 1 wherein said bearing includes an elongated sleeve having a generally cylindrical passage extending therethrough and said shaft extends completely through said passage and the sleeve is between the end wall and the driving portion in said axial position.

11. A trephine as defined in claim 1 wherein said cutting edge is formed from a diamond and said mounting means includes a mounting body of adhesive retained on said shaft and said blade is fixedly embedded in the mounting body.

12. A trephine as defined in claim 1 wherein the blade lies entirely within the perimeter of the peripheral wall as viewed in a direction perpendicular to the end wall.

13. A trephine as defined in claim 1 wherein said blade projects perpendicularly beyond said end wall no more than about 0.41 mm.

14. A trephine as defined in claim 1 wherein said bearing has outer and inner ends, said shaft is axially slidable in the passage from the outer end of the bearing to said axial position and is axially slidable from said axial position toward the outer end of the bearing to remove the shaft from the bearing.

15. A trephine as defined in claim 1 wherein the bearing includes an elongated sleeve having outer and inner ends and a cylindrical passage extending longitudinally through the sleeve, said shaft being receivable in said passage from said outer end and slidable axially and rotatable therein.

16. A trephine for cutting a groove in the cornea of an eye, said trephine comprising:
a fixation member including a bearing and means cooperable with the eye for fixing the fixation member to the eye;
first and second shafts, each of said shafts having a peripheral wall, an end wall, and a driving portion for use in rotating the associated shaft;
first and second blades;
means for mounting the first and second blades on the first and second shafts, respectively, with the blades projecting from their respective shafts;
said first and second shafts being sequentially releasably receivable in said bearing for rotation relative to the fixation member; and
said first blade having a first orientation with respect to the axis of the first shaft and the second blade having a second orientation with respect to the axis of the second shaft, said first and second orientations being different whereby the cut formed by the blade of the first shaft is different from the cut formed by the blade of the second shaft to tend to enable a segment to be severed from the cornea to form the groove.

17. A trephine as defined in claim 16 wherein said bearing has a peripheral wall and a passage extending through the bearing for receiving the shaft, said bearing has inner and outer ends and said peripheral wall only partially circumscribes said passage at an outer end portion of the bearing.

18. A trephine for making a cut in the cornea of an eye, said trephine comprising:
a fixation member including a bearing and means cooperable with the eye for fixing the fixation member to the eye;
said bearing including a sleeve having inner and outer ends;
a shaft having a peripheral wall, an end wall and a driving portion for use in rotating the shaft;
a blade having a cutting edge;
means for mounting the blade on the shaft with the cutting edge at least partially exposed, said shaft with the blade therein being insertable into the sleeve;
a segment of said sleeve at said outer end being removed to permit insertion of the shaft into the sleeve with reduced likelihood of damage to the blade;
said shaft being rotatable in said sleeve about a rotational axis to cause the blade to form a cut in the cornea; and
said fixing means including a plurality of legs coupled to the sleeve and adapted to extend toward the sclera radially outwardly of the sleeve and said legs terminating in a plurality of teeth engageable with the sclera.

19. A trephine as defined in claim 18 including a plurality of webs for coupling the legs to the sleeve, respectively.

20. A method of making at least one cut in the cornea of the eye comprising:
providing a fixation member with the fixation member having a bearing with inner and outer ends and a passage extending therethrough;
affixing the fixation member to the eye with the passage extending toward the cornea;
providing a first shaft having an end wall and a first blade with the blade being oriented with respect to the shaft so that it can make a cut in the cornea;
inserting the first shaft into the bearing to a first axial position in which the end wall of the first shaft and the first blade are in contact with the cornea;
rotating the first shaft when the first shaft is in said first axial position in said bearing to form a first cut in the cornea.

21. A method as defined in claim 20 wherein said step of affixing places the inner end of the bearing into contact with the cornea and said first-mentioned step of inserting pushes the cornea away from the inner end of the bearing.

22. A method as defined in claim 20 wherein said step of affixing includes affixing the fixation member to the sclera.

23. A method as defined in claim 20 including providing a second shaft having an end wall and, said second shaft having a second blade, said blades being oriented with respect to their associated shafts so that they can cooperate to cut a groove in the cornea, withdrawing the first shaft from the bearing, inserting the second shaft into the bearing to a second axial position in which the end wall of the second shaft and the second blade are in contact with the cornea, rotating the second shaft when the second shaft is in said second axial position in said bearing to form a second cut in the cornea to tend to define a segment of the cornea which may be removed to define a groove.

24. A knife for use with a fixation member for making a cut in the cornea of the eye, said knife comprising:
an elongated shaft having a peripheral wall and a longitudinal axis, an end wall and a driving portion for use in rotating the shaft;
a blade having a cutting edge;
a mounting body for affixing the blade to the shaft with the blade being embedded in the mounting body and with the cutting edge exposed and projecting from and beyond the end wall, the portion of said blade which projects beyond the end wall lying entirely within the perimeter of the peripheral wall as viewed in a direction perpendicular to the end wall and said cutting edge being radially spaced from said axis; and at least the portion of said blade which projects beyond the end wall being inclined relative to said axis.

25. A knife as defined in claim 24 wherein the blade is adjacent the peripheral wall and the projecting portion of said blade is inclined radially inwardly of the shaft.

26. A knife as defined in claim 24 wherein the projecting portion of said blade is inclined radially outwardly as it extends toward the cutting edge, said cutting edge being adjacent said peripheral wall.

27. A knife as defined in claim 24 wherein at least the projecting portion of said blade is constructed in a diamond.

28. A knife as defined in claim 24 wherein the blade projects no more than about 0.41 mm beyond the end wall.

29. A knife as defined in claim 24 wherein said shaft has a groove opening in the end wall and said mounting body is retained in said groove.

30. A trephine for making a cut in the cornea of an eye, said trephine comprising:

a fixation member including a bearing having a passage extending therethrough and means cooperable with the eye for fixing the fixation member to the eye;

a shaft having a peripheral wall, an end wall and a driving portion for use in rotating the shaft;

a blade having a cutting edge;

means for mounting the blade on the shaft with the blade projecting a fixed distance beyond the end wall and with the cutting edge at least partially exposed;

said shaft being rotatable in said passage about a rotational axis and axially slidable in said passage; and the shaft being positionable in the bearing in an axial position in which the end wall is engageable with the cornea and the driving portion can be driven whereby the shaft can be rotated in said axial position to cause the blade to form a cut in the cornea having a depth which is related to said fixed distance.

31. A trephine as defined in claim 30 wherein said shaft is releasably receivable in said passage and can be freely slid axially in the passage to remove the shaft from the bearing.

32. A trephine as defined in claim 30 wherein the shaft has a longitudinal axis and the blade is elongated and inclined relative to the longitudinal axis of the shaft.

33. A trephine as defined in claim 30 wherein said cooperating means includes teeth on the fixation member located to engage the sclera of the eye and cooperate therewith to fix the fixation member to the eye.

* * * * *